(12) United States Patent
Sendijarevic

(10) Patent No.: US 6,881,486 B2
(45) Date of Patent: Apr. 19, 2005

(54) WATER CURABLE CASTING TAPES AND METHODS OF PREPARING THE SAME

(75) Inventor: Aisa Sendijarevic, Troy, MI (US)

(73) Assignee: Troy Polymers, Inc., Troy, MI (US)

( * ) Notice: Subject to any disclaimer, the term of this patent is extended or adjusted under 35 U.S.C. 154(b) by 32 days.

(21) Appl. No.: 10/602,381

(22) Filed: Jun. 24, 2003

(65) Prior Publication Data

US 2003/0235692 A1 Dec. 25, 2003

Related U.S. Application Data

(60) Provisional application No. 60/390,951, filed on Jun. 24, 2002.

(51) Int. Cl.$^7$ .................. B32B 13/00; B32B 13/04; B32B 13/12; B32B 13/14; A61F 5/00
(52) U.S. Cl. .................. 428/425.5; 428/423.1; 428/702; 428/703; 442/42; 442/44; 442/58; 442/256; 442/279; 442/286; 442/386; 442/394; 602/6; 602/8
(58) Field of Search .................. 428/423.1, 425.5, 428/702, 703; 442/42, 44, 58, 255, 256, 279, 286, 386, 394; 602/68

(56) References Cited

U.S. PATENT DOCUMENTS

| | | |
|---|---|---|
| 4,433,680 A * | 2/1984 | Yoon ............... 602/8 |
| 4,502,479 A | 3/1985 | Garwood et al. |
| 4,643,909 A | 2/1987 | Kammerer |
| 4,655,208 A * | 4/1987 | Yoon ............... 602/8 |
| 4,667,661 A | 5/1987 | Scholz et al. |
| 4,668,563 A | 5/1987 | Buese et al. |
| 4,683,877 A | 8/1987 | Ersfeld et al. |
| 4,690,842 A | 9/1987 | Kammerer et al. |
| 4,934,356 A * | 6/1990 | Klintworth, Jr. ............... 602/8 |
| 5,061,555 A | 10/1991 | Edenbaum et al. |
| 5,244,997 A | 9/1993 | Scholz et al. |
| 5,480,708 A | 1/1996 | Cheng |
| 5,527,286 A | 6/1996 | Lekhgolts et al. |
| 5,725,487 A | 3/1998 | Freeman et al. |
| 5,823,978 A | 10/1998 | Cueman et al. |
| 5,885,234 A | 3/1999 | Sandvig et al. |
| 5,931,798 A | 8/1999 | Green et al. |
| 5,944,674 A | 8/1999 | Richard et al. |
| 5,976,610 A | 11/1999 | Scholz et al. |
| 5,984,884 A | 11/1999 | Alvarez et al. |
| 5,997,492 A | 12/1999 | Delmore et al. |
| 6,077,240 A | 6/2000 | Sholz et al. |
| 6,100,206 A * | 8/2000 | Scholz et al. ............... 442/42 |

* cited by examiner

*Primary Examiner*—Vivian Chen
(74) *Attorney, Agent, or Firm*—Brooks Kushman PC

(57) ABSTRACT

One aspect of the present invention is a casting article comprised of a water-curable Plaster of Paris (PP) article having a first side and a second side and having a substrate and PP material and a polyisocyanate material being applied to at least one of the first and second sides of the water-curable PP to obtain a water-curable hybrid plaster-polyisocyanate (HPP) casting article.

37 Claims, 3 Drawing Sheets

WATER CURABLE CASTING TAPES AND METHODS OF PREPARING THE SAME

CROSS-REFERENCE TO RELATED APPLICATION

This application claims the benefit of U.S. provisional application Ser. No. 60/390,951, filed Jun. 24, 2002, and entitled "Water Curable Casting Tapes and Methods of Preparing The Same".

BACKGROUND OF THE INVENTION

1. Field of the Invention

One aspect of the present invention generally relates to water curable casting tapes and methods of preparing the same.

2. Background Art

There are various types of immobilization tapes and splints available on the market and described in patent literature, but the most widely used are Plaster of Paris tapes and the polyisocyanate tapes. Plaster of Paris casting tapes are basically gauzes (or some other meshed tapes) impregnated with gypsum. They are activated by immersion in water for about a few seconds, and then applied to immobilize joints or fractures before they set hard. The time needed for them to set hard is defined as the set-time, and it can range from about 5 to about 20 minutes depending on the additives present in Plaster of Paris. Despite many deficiencies, Plaster of Paris immobilization tapes are still widely utilized due to their low cost and good moldability. Their main disadvantages are relatively poor strength to weight ratio that results in bulky and heavy casts, and relatively poor resistance to water that restrict contact with water. In addition, Plaster of Paris tapes often have poor air permeability, which often causes skin irritation.

More recently, synthetic reactive polyurethane casting tapes were developed, which are comprised of a NCO-polyurethane prepolymer (and additives) coated onto mesh-tape (fiberglass, polyester, etc). These tapes are also activated by immersion in water, which reacts with isocyanate (usually in the presence of catalyst) with the set-time of typically about 3 to about 6 minutes. Cured polyisocyanate casts typically have good resistance to water and significantly higher strength to weight ratio than Plaster of Paris tapes. However, they are typically more expensive than Plaster of Paris immobilization tapes. Other disadvantages include that the reaction of isocyanate and water is exothermic, which may cause burns, shelf instability (due to sensitivity of isocyanate to moisture), and somewhat inferior moldability than that of the Plaster of Paris immobilization tapes.

In light of the foregoing, there is a need for orthopedics immobilization casts that combine good properties of Plaster of Paris casts, i.e. good moldability, and good properties of isocyanate casts, i.e. good strength to weight ratio and resistance to water.

SUMMARY OF THE INVENTION

One aspect of the present invention is a casting article comprised of a water-curable Plaster of Paris (PP) article having a first side and a second side and having a substrate and PP material and a polyisocyanate material being applied to at least one of the first and second sides of the water-curable PP to obtain a water-curable hybrid plaster-polyisocyanate (HPP) casting article. In certain embodiments, the water-curable HPP casting article can be cured.

The first side of the water-curable PP article can be smoother than the second side and the polyisocyanate material is applied to the first side. Additionally, the water-curable PP article can be a water-curable PP casting tape or a water-curable PP splint and the polyisocyanate material can be a polyisocyanate tape or a polyisocyanate resin. The substrate for the PP article can be selected from the group consisting of cotton, glass fiber, polymeric knit, woven material and non-woven material. The weight ratio of the polyisocyanate material to the water-curable PP article can be in the range of about 1:99 to about 99:1. The polyisocyanate material can be selected from the group consisting of aromatic isocyanates, aliphatic isocyanates, cycloaliphatic isocyanates, isocyanate-based adducts, isocyanate-based derivatives, NCO-prepolymers, NCO-oligomers and NCO-quasi prepolymers. The polyisocyanate material can have an isocyanate to active hydrogen equivalent weight ratio of greater than about 1.

The polyisocyanate material can be cured without a catalyst that promotes the reaction of the polyisocyanate material and water. Alternatively, the polyisocyanate material can be cured with at least one catalyst promoting the reaction of the polyisocyanate material and water. The PP material can include the baked product of a PP paste and the at least one catalyst can be added to the PP paste. The at least one catalyst does not significantly interfere with the curing of the water-curable PP article. The water-curable PP article can include at least one hardening agent and the polyisocyanate material can include at least one antifoaming agent and at least one stabilizer.

Another aspect of the present invention is a casting assembly comprised of a water-curable Plaster of Paris (PP) tape having a first side and a second side and having a substrate and PP material and a polyisocyanate tape having a substrate and a polyisocyanate resin. The water-curable PP tape and the polyisocyanate tape can be contacted to obtain a water-curable hybrid plaster-polyisocyanate (HPP) casting article. In certain embodiments, the water-curable HPP casting article can be cured.

The casting assembly can further include a pouch for at least partially containing the water-curable PP tape and the polyisocyanate tape. The casting assembly can further include a foil material for at least partially separating the water-curable PP tape and the polyisocyanate tape in the pouch. The water curable PP tape and polyisocyanate tape can be dry packaged to minimize exposure to water and/or moisture. The water-curable PP tape and/or the polyisocyanate tape can be commercially available and/or can be specially designed.

The substrate for the water-curable PP tape can be selected from the group consisting of cotton, glass fiber, polymeric knit, woven material and non-woven material. The substrate for the polyisocyanate tape can be selected from the group consisting of cotton, glass fiber, polymeric knit, woven material and non-woven material. The weight ratio of the polyisocyanate tape and the water-curable PP tape can be in the range of about 1:99 to about 99:1. The polyisocyanate resin can be selected from the group consisting of aromatic isocyanates, aliphatic isocyanates, cycloaliphatic isocyanates, isocyanate-based adducts, isocyanate-based derivatives, NCO-prepolymers, NCO-oligomers and NCO-quasi prepolymers. The polyisocyanate tape can have an isocyanate to active hydrogen equivalent weight ratio of greater than about 1.

The polyisocyanate tape can be cured without a catalyst that promotes the reaction of the polyisocyanate tape and water. Alternatively, the polyisocyanate tape can be cured with at least one catalyst for promoting the reaction of the polyisocyanate tape and water. The PP tape can include the baked-product of a PP paste and the at least one catalyst can be added to the PP paste. The at least one catalyst does not significantly interfere with the curing of the water-curable PP tape. The water-curable PP tape can include at least one hardening agent and the polyisocyanate material can include at least one antifoaming agent and at least one stabilizer.

Yet another aspect of the present invention relates to a method for preparing a cured hybrid plaster-polyisocyanate (HPP) casting article. The method is comprised of providing a water-curable Plaster of Paris (PP) material having a first side and a second side and being comprised of a substrate and a PP material and a polyisocyanate material, applying the polyisocyanate material to at least one of the first and second sides of the water-curable PP article to obtain a water-curable hybrid plaster-polyisocyanate (HPP) casting article, and curing the water-curable hybrid plaster-polyisocyanate (HPP) casting article to obtain a cured HPP casting article.

The applying step can be comprised of spraying or coating the polyisocyanate material onto the water-curable PP article. The method can further include providing a PP article and baking the PP material to obtain the water-curable PP article. The method can further include adding at least one catalyst for promoting the reaction of isocyanates with water to the PP article prior to the baking step. Alternatively, the method can include adding at least one catalyst for promoting reaction of isocyanates with water to the polyisocyanate material during the baking step. The water-curable PP article can be comprised of a water-curable PP tape and the polyisocyanate material can be comprised of a polyisocyanate tape. The applying step can be comprised of laminating the polyisocyanate tape onto the water-curable PP tape.

In certain embodiments, the water-curable PP material can be comprised of at least a first and second PP layer and the polyisocyanate material can be comprised of at least a first and second polyisocyanate layer. The method can further include, prior to the curing step, applying the first polyisocyanate layer to the first PP layer, applying the second PP layer to the first polyisocyanate layer, and applying the second polyisocyanate layer to the second PP layer.

The above embodiments and other embodiments, features, and advantages of the present invention are readily apparent form the following detailed description of the best mode for carrying out the invention.

BRIEF DESCRIPTION OF THE DRAWINGS

The features of the present invention which are believed to be novel are set forth with particularity in the appended claims. The present invention, together with further objects and advantages thereof, may be best understood with reference to the following description, taken in connection with the accompanying drawings:

DETAILED DESCRIPTION OF EMBODIMENTS OF THE PRESENT INVENTION

Figure 1:
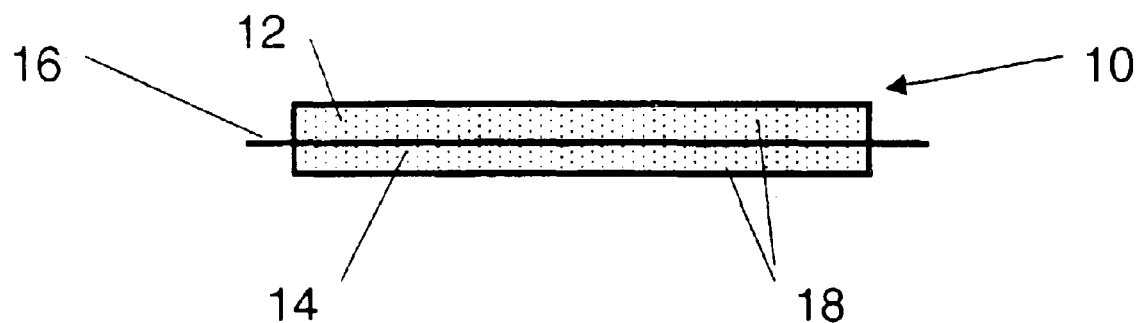
FIG. 1 is an illustration of a cross-sectional view of a Plaster of Paris casting tape with two sides, containing a substrate onto which Plaster of Paris is applied.

As required, detailed embodiments of the present invention are disclosed herein. However, it is to be understood that the disclosed embodiments are merely exemplary of the invention that may be embodied in various and alternative forms. Therefore, specific functional details disclosed herein are not to be interpreted as limiting, but merely as representative basis for teaching one skilled in the art to variously employ in the present invention.

One aspect of the present invention is a hybrid plaster-polyisocyanate (HPP) orthopedic immobilization casting tapes (and casting articles) and methods of preparing these tapes, that can be activated by immersion in water. It should be understood that the HPP casting tapes of the present invention can be used in casting articles, for example splints. To prepare a HPP casting tape, Plaster of Paris (PP) tapes can be modified by adding to them at least one layer of varying amounts of polyisocyanates, which can impart to the Plaster of Paris some properties of polyurethane casting tapes such as improved strength to weight ratio, resistance to water, and air permeability. Upon immersion in water, the isocyanate can laminate or bind plaster layer(s) and thus reinforce the whole cast. Other benefits resulting from the addition of polyisocyanate layers to PP can include improved green strength and decreased dripping as compared to Plaster of Paris tapes. Improved strength to weight ratio over conventional Plaster of Paris can allow for the reduction of overall cast weight.

Another aspect of the present invention provides several methods for the modification of Plaster of Paris tapes with reactive polyisocyanate resin to produce HPP immobilization tapes and casting articles. By dipping HPP casting tapes in water, plaster can cure along with the polymerization of isocyanate through reaction with water, which binds and reinforces the plaster. Plaster of Paris immobilization tapes can be made by coating a paste of Plaster of Paris and water onto gauze (or other meshed fabrics such as polyester, polypropilene, etc.) which can then be baked at elevated temperature to remove excess water. In certain embodiments, the reactive isocyanate (or NCO-prepolymer) is not added to a paste of Plaster of Paris or Plaster of Paris and water slurry, because polyisocyanate will react with water at elevated temperatures during baking of Plaster of Paris. The present invention provides methods for modification of Plaster of Paris tapes by application of reactive polyisocyanate to fully baked Plaster of Paris tapes, resulting in HPP tapes and casting articles.

According to one method of the present invention for making HPP casting tapes, polyisocyanate resin can be applied onto a baked Plaster of Paris tape by spraying or some other coating method known to one of ordinary skill in the art, such as transfer coating. To improve shelf stability, HPP casts should be packaged in a way to minimize exposure to water, as is typically done for isocyanate tapes and splints, Plaster of Paris tapes and splints, and/or according to any other dry packaging technique.

FIG. 1 is an illustration of a cross-sectional view of water-curable PP casting 10 with first and second sides 12 and 14 containing substrate 16 onto which Plaster of Paris is applied. Plaster of Paris tape substrate 16 can be, but is not limited to, cotton, polymeric knit or glass fiber. Plaster of Paris tape substrate 16 can be woven or non-woven substrates, of different dimensions and geometries, and with varying loadings of Plaster on the substrate, without additives or with hardening additive(s) for Plaster of Paris, and in certain embodiments, with catalyst(s) for isocyanate reaction with water and/or hardening additive(s) for Plaster of Paris.

Figure 2:
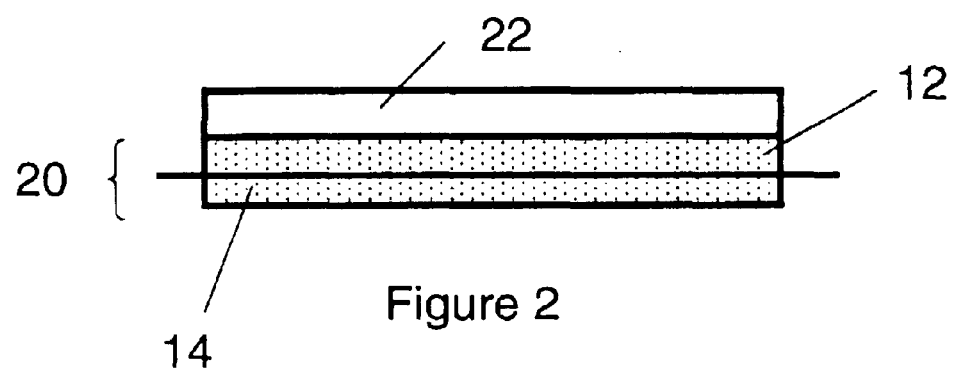
FIG. 2 is an illustration of cross-sectional view of a casting assembly in accord with one embodiment of the present invention.
Figure 3:
FIG. 3 is an illustration of cross-sectional view of a casting assembly in accord with one embodiment of the present invention.

FIG. 2 is an illustration of a cross-sectional view of one embodiment of the present invention that includes PP casting tape 20 and isocyanate resin 22 applied on first side 12 of the PP casting tape. In certain embodiments, isocyanate resin can be applied on only second side 14 of the PP casting tape. In yet other embodiments, isocyanate resin 24 can be applied on both sides of PP casting tapes as illustrated in FIG. 3.

Polyisocyanates that can be used in accordance with the present invention include, but are not limited to, aromatic, aliphatic, and cycloaliphatic isocyanates, isocyanate-based adducts and derivatives, the NCO-oligomers, prepolymers and quasi prepolymers made by reaction of isocyanates with polyols and/or polyamines with isocyanate to active (reactive) hydrogen equivalent weight ratio greater than about 1, or between about 2 and about 20, and more specifically between about 2 and about 10, or a mixture there of, or copolymers there of. The polyols and polyamines can be selected from, but are not limited to, polyethers, polyesters, polycarbonates, and hydrocarbons, or a mixture there of, or copolymers there of, with average functionality higher than about 1, or between about 2 and about 8, and more specifically between about 2 and about 4. In certain embodiments, NCO-prepolymers and quasi-prepolymers are utilized.

The weight ratio of polymeric isocyanate to Plaster of Paris can be in the range between about 1:99 and about 99:1, in certain embodiments, between about 1:49 and about 1:2, and in other embodiments between about 1:49 and about 1:4. The HPP casting tapes prepared in accordance with the present invention can be cured without any catalyst that promotes the reaction of isocyanate with water. In certain embodiments, the HPP casting tapes can include catalyst(s) for the reaction of isocyanate with water. In other embodiments, the catalyst for the reaction of isocyanate with water can be added to the Plaster of Paris. The catalyst(s) for the reaction of isocyanate with water can be added to the Plaster of Paris before, during or after baking of Plaster of Paris, prior or after addition of the isocyanate to Plaster of Paris. By the addition of catalyst for the reaction of isocyanate with water to the Plaster of Paris instead to polyisocyanate, the shelf stability of the HPP casting tape can be increased. In certain embodiments, the catalyst for the reaction of isocyanate with water does not interfere with curing of Plaster, and does not affect the moldability of the HPP casting.

Antifoaming agent(s) can be added to the polyisocyanate to prevent or minimize the bubble formation, to improve strength, and/or adhesion properties of the polymeric isocyanate. In order to maximize the shelf stability of the HPP casting tapes, the stabilizers, such as benzoil chloride, can be added to the polymeric isocyanate.

According to another method of making HPP casting tapes, Plaster of Paris tapes and polyisocyanate tapes can be prepared separately, packaged into the same (one) or separate pouches (two) and combined before packaging, or before dipping, or during or after dipping in the water, or at any point before the end of cure time.

Figure 4:
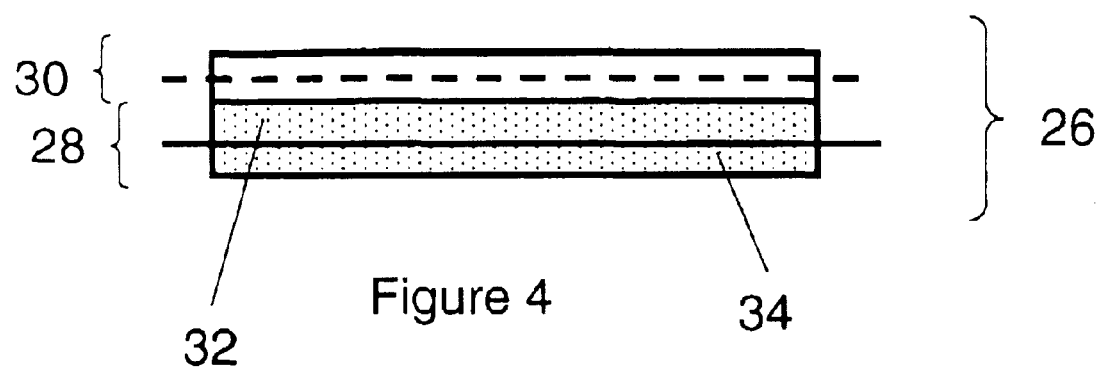
FIG. 4 is an illustration of cross-sectional view of a casting assembly in accord with one embodiment of the present invention.

FIG. 4 is an illustration of a cross-sectional view of a casting assembly in accord with one embodiment of the present invention. According to FIG. 4, HPP casting assembly 26 includes Plaster of Paris casting tape 28 and polyisocyanate tape 30 applied to first side 32 of Plaster of Paris casting tape 28. Polyisocyanate tape can also be applied to second side 34 of Plaster of Paris tape or both sides of Plaster of Paris tape.

Figure 5:
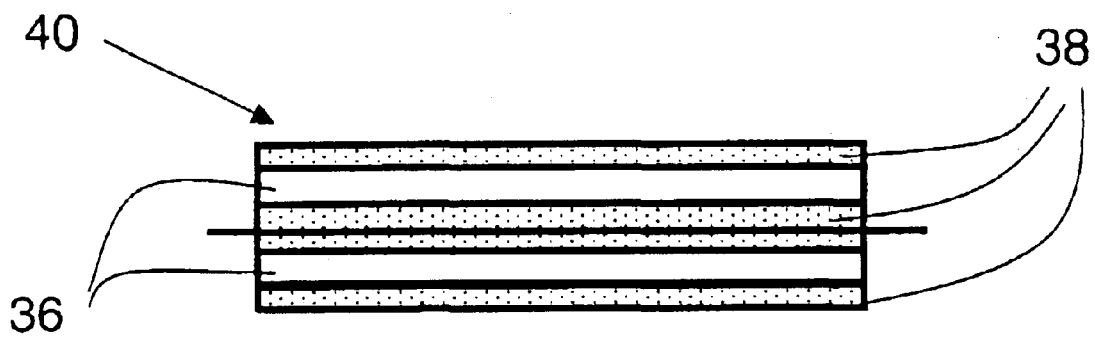
FIG. 5 is an illustration of cross-sectional view of a casting assembly in accord with one embodiment of the present invention.

In certain embodiments, several layers of polyisocyanate resin 36 and PP casting tapes 38 can be combined to form HPP casting article 40, as illustrated in FIG. 5. Alternatively, several layers of isocyanate tapes and PP casting tapes can be layered to form HPP casting articles.

Figure 6:
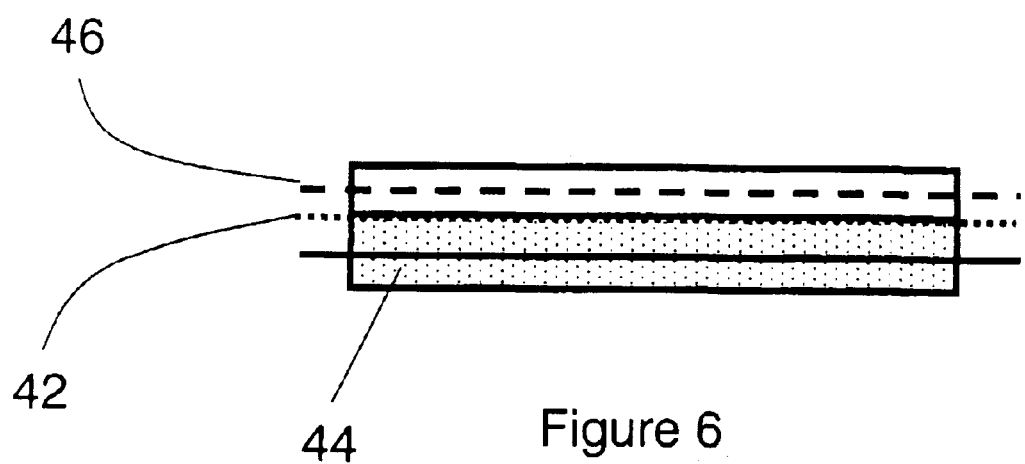
FIG. 6 is an illustration of a cross-sectional view of a casting assembly in accord with one embodiment of the present invention, incorporating a foil for packaging purposes.
Figure 7:
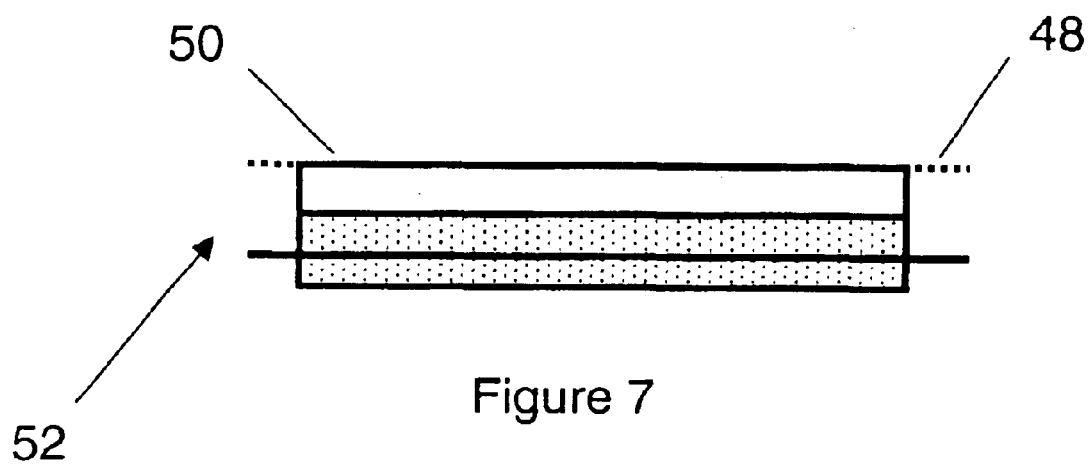
FIG. 7 is an illustration of a cross-sectional view of a casting assembly in accord with one embodiment of the present invention, incorporating a foil for packaging purposes.

PP casting tape and polyisocyanate tape can be inserted and contained (packaged) into one pouch or separate pouches. Optionally, for packaging purposes, foil 42 and more specifically a release foil can be placed in between PP casting tape 44 and isocyanate tape 46 to separate the two, as illustrated in FIG. 6. Alternatively, foil 48 can be placed on first side 50 of HPP casting article or tape 52, as illustrated in FIG. 7, or foil can be placed on all or any sides of HPP tapes or casting articles. The foil can be removed before dipping or during dipping in water or at any point before the end of cure time.

In HPP tapes and casting articles, the PP tapes and isocyanate tapes can be of same or different number, dimensions, and geometries. If foil is used in packaging, it can be of same or different number, dimension, and geometries as HPP tapes.

Numerous types of Plaster of Paris tapes and polyisocyanate tapes are commercially available (3M, Johnson & Johnson, DeRoyal, etc.) and can be used as such as components of the HPP castings. In certain embodiments, these tapes can be packaged in one pouch. In other embodiments, these tapes can be specially designed and manufactured for HPP castings. The Plaster of Paris tape substrate can be, but is not limited to, cotton, polymeric knits and glass fiber. The Plaster of Paris tape substrate can be woven or non-woven substrates (tapes), with different dimensions and geometries of the tape, with various loadings of Plaster on the tape, without additives or with hardening additive(s) for Plaster of Paris, and in certain embodiments, with hardening additive (s) for Plaster of Paris and catalyst(s) for isocyanate reaction with water and/or hardening additive(s) for Plaster of Paris.

The polyisocyanate tapes can be composed of substrates that can be selected from, but is not limited to, the following group: cotton, polymeric knits, and glass fiber, woven or non-woven substrates (tapes), and different types of polyisocyanates, with different dimensions and geometries of the tape, at different loadings of polyisocyanates on the tape, with catalyst(s) for reaction of isocyanates with water and stabilizer(s), and in certain embodiments, without catalyst(s) for reaction of isocyanates with water and with stabilizer(s), such as benzoil chloride.

When packed in one pouch, the Plaster of Paris and polyisocyanate tapes can be aligned with each other or separated by foil, more specifically release foil. The weight ratio of polymeric isocyanate to Plaster of Paris can be in the range between about 1:99 and about 99:1, in certain embodiments, between about 5:95 and about 95:5, in other embodiments, between about 5:95 and about 9:1, and in yet other embodiments, between about 5:95 and about 1:1. The HPP casting tapes prepared with this method of the present invention can be cured without any catalyst that promotes the reaction of isocyanate with water. In certain embodiments, the HPP casting tapes can include catalyst(s) for the reaction of isocyanate with water. In certain embodiments, the catalyst(s) for reaction of isocyanates with water can be added to the Plaster of Paris tape. The catalyst (s) can be added to the Plaster of Paris before, during or after baking, prior or after combining the Plaster of Paris tape with polyisocyanate tape. By addition of the catalyst to the Plaster of Paris, the shelf stability of the polyisocyanate tape can be improved. In certain embodiments, the catalyst does not interfere with curing of Plaster of Paris, and does not affect the moldability of the HPP casting.

Polyisocyanates that can be used according to the present invention include, but are not limited to, aromatic, aliphatic, cycloaliphatic isocyanates, isocyanate-based adducts and derivatives, and the NCO-oligomers, prepolymers and quasi prepolymers made by reaction of isocyanates with polyols or polyamines with isocyanate to active (reactive) hydrogen equivalent weight ratio larger than about 1, in certain embodiments, between about 2 and about 20, and in other embodiments, between about 2 and about 10, or a mixture there of, or copolymers there of. The polyols and polyamines can be selected from, but are not limited to, polyether, polyester, polycarbonate and hydrocarbon, or a mixture there of, or copolymers there of, with average functionality higher than about 1, in certain embodiments, between about 2 and about 8, and in other embodiments, between about 2 and about 4. In certain embodiments, NCO-prepolymers and quasi-prepolymers can be used.

Antifoaming agent(s) can be added to the polyisocyanate to prevent or minimize the bubble formation, to improve strength, and adhesion properties of the polymeric isocyanate. In order to maximize the shelf stability, the stabilizers such as benzoil chloride can be added to the polymeric isocyanate.

EXAMPLE 1

33.1 g of Plaster of Paris (Customs Building Products) was mixed with a spatula with 16.5 g of water and transferred to the flat glass plate. The set-time was determined by applying the cylindrical wooden rod to the paste. The time when no impression was observed after applying the cylindrical wooden rod to the paste was recorded as the set-time. The set-time was 20 minutes.

EXAMPLE 2

32.6 g of Plaster of Paris (Custom® Building Products) was blended with 0.49 g of $K_2SO_4$ (potassium sulfate) by using a Speed Mixer machine (2000 rpm, 1 minute). $K_2SO_4$ was added to accelerate the set time of Plaster of Paris. The blend was mixed with 16.5 g of water and the set-time was determined (as described in Example 1) to be approximately between 4 and 5 minutes.

EXAMPLE 3

36.2 g of Plaster of Paris (Custom® Building Products), 0.49 g of potassium sulfate and 0.0163 g of a catalyst for reaction of isocyanate with water (Dabco Crystalline, Air Product) were blended by using a Speed Mixer machine (2000 rpm, 1 minute). The blend was mixed with 16.5 g of water, and the set-time that was determined (as described in Example 1) to be 4 minutes. This is an indication that this catalyst at this concentration does not impede the curing (setting-time) of Plaster of Paris.

EXAMPLE 4

36.2 g of Plaster of Paris (Custom® Building Products), 0.49 g of potassium sulfate and 0.0326 g of Dabco Crystalline were blended by using a Speed Mixer machine (2000 rpm, 1 minute). The blend was mixed with 16.5 g of water, and the set-time was determined (as described in Example 1) to be 4 minutes. At the higher concentration of Dabco Crystalline catalyst than those in Example 3, the curing (setting-time) of Plaster of Paris was not affected.

EXAMPLE 5

36.2 g of Plaster of Paris (Custom® Building Products), 0.49 g of potassium sulfate and 0.163 g of of Dabco Crystalline were blended by using a Speed Mixer machine (2000 rpm, 1 minute). The blend was mixed with 16.5 g of water, and the set-time determined (as described in Example 1) be 3.5 minutes. The setting-time (curing) of Plaster of Paris slightly decreased at higher concentration of Dabco Crystalline catalyst than those in Examples 3 and 4.

EXAMPLE 6

12 inches long and 4.1 inches wide (18.0 g) of Plaster of Paris tape (gauze substrate) (Type A) was cut from the pouch, dipped in water for 5 seconds and then was wound and cast around a glass tube. After one hour the cured casts were taken off of a glass tube and allowed to dry at ambient conditions for 24 hours. The weight of cured (dry) cast was 15.8 g indicating weight loss during dipping in water for 5 seconds (Table 1). Afterwards, the cured cast was immersed in water and weight changes were recorded after 2 and 24 hours (Table 1). After immersion in water for 2 hours, the weight of the cast increased by 27%. By prolonged immersion in water for 24 hours, the weight of the cast decreased somewhat compared to the weight after 2 hours of immersion, which is an indication of material loss. The cast was soft after immersion in water for 24 hours in contrast to the original cast that was rigid before immersion in water (0 hours).

EXAMPLE 7

0.7 g of polyisocyanate (3.7% based on weight of Plaster of Paris tape) was coated with a small spatula onto backside of 12 inches long and 4.1 inches wide (18.0 g) of Plaster of Paris tape (Type A). The polyisocyanate was NCO-quasi prepolymer with isocyante to polyol equivalent weight ratio of 4.8/1. The NCO-quasi prepolymer was prepared by reacting 50 g of polymeric isocynate (PAPI 2094, Dow) and 31 g of Pluracol P-710 (BASF). After coating with polyisocyanate, the tape was dipped in water for 5 seconds, wound and cast around a glass tube and treated and tested as described in Example 6. The initial weight of the tape before immersion in water and curing was 18.7 g. The weight of the cured tape was 19.2 g (Table 1). No significant change in weight of the tape was observed by dipping in water and curing which is contrary to the cured non-modified Plaster of Paris cast from Example 6 where significant weight loss was recorded (Table 1). After 2 hours of immersion in water, the weight increase in the modified tape in this example was somewhat lower (20%) compared to that of the non-modified tape (27%) from Example 6. Upon prolonged immersion for 24 hours the weight did not changed significantly and the cast was rigid (Table 1). This example demonstrates that the addition of a small amount of polyisocyanate to Plaster of Paris cast improves the water resistance of the Plaster of Paris cast and therefore its mechanical integrity in wet conditions.

EXAMPLE 8

1.2 g of polyisocyanate (6.7% based on weight of Plaster of Paris tape) was coated onto the backside of 12 inches long and 4.1 inches wide (18.0 g) of Plaster of Paris tape (Type A). The polyisocyanate was NCO-quasi prepolymer with isocyanate to polyol equivalent weight ratio of 4.8/1. The quasi prepolymer was prepared by reacting 50 g of polymeric isocyanate (PAPI 2094, Dow) and 31 g of Pluracol P-710 (BASF). After coating with polyisocyanate, the tape was dipped in water for 5 seconds, wound and cast around a glass tube and treated and tested as described in Examples 6 and 7. Upon immersion in water, this cast behaved similarly to Plaster of Paris cast modified with polyisocyanate in Example 7 (Table 1). Table 1 includes the properties of Plaster of Paris (PP) cast and HPP casts upon immersion in water. The (a) represents an incremental Wt. % change.

glass tube, and the compressive strength of the cast was measured after 24 hours of aging (Table 2). Table 2 includes compressive properties of 24 hours cured Plaster of Paris casts.

EXAMPLE 11

The cast of the Plaster of Paris tape (Type B) was prepared by dipping in water 20 inches long and 3 inches wide (18 g) tape for 5 seconds, wound and cast around glass tube, and the compressive strength was measured after 24 hours of aging (Table 2).

TABLE 2

| Designation | Example 9 | Example 10 | Example 11 |
|---|---|---|---|
| Type of cast | HPP | HPP | PP |
| Composition (pbw) | | | |
| Plaster of Paris tape, type B | 18 | 18 | 18 |
| Polyisocyanate | 1.5 | 1.5 | 0 |

TABLE 1

| Sample Design | Type of Cast | Initial Weight (g) | Weight Cured Tape (g) | % Weight Change After Curing (a) | Weight After 2 Hrs In Water (g) | % Weight Change After 2 Hrs In Water (a) | Weight After 24 Hrs In Water (g) | % Weight Change After 24 Hrs In Water (a) | Mechanical Property |
|---|---|---|---|---|---|---|---|---|---|
| Ex. 6 | PP | 18.0 | 15.8 | −12% | 20.1 | 27% | 18.1 | −10% | Soft |
| Ex. 7 | HPP w/ 0.7 g NCO prepolymer | 18.7 | 19.2 | 3% | 23.1 | 20% | 23.4 | 1% | Rigid |
| Ex. 8 | HPP w/ 1.2 g NCO prepolymer | 19.2 | 18.9 | 2% | 22.6 | 19.2% | 22.8 | 1% | Rigid |

EXAMPLE 9

1.5 g of polyisocyanate (8.3% based on weight of Plaster of Paris tape) was coated on the back side of the 20 inches long and 3 inches wide (18 g) of the Plaster of Paris tape (Type B). The polyisocyanate was an NCO-quasi prepolymer with isocyanate to polyol equivalent ratio of 4.8/1, containing a small amount of tertiary amine catalyst, less than 0.05% based on weight of polyisocyanate. The quasi prepolymer was prepared by reacting 51 g of polymeric isocyanate PAPI 2094 and 30 g of polycaprolactone diol TONE 32C8 (equivalent weight 371.8, Dow Chemical). After coating with polyisocyanate, the HPP tape was dipped in water for 5 seconds, wound and cast around glass tube. After 24 hours, the compressive strength (at 2, 5, 10 and 20% compression) of the cast was measured by an INSTRON Universal Testing Instrument Model 1122, Table 2.

EXAMPLE 10

1.5 g of polyisocyanate (8.3% based on weight of Plaster of Paris tape) was coated on the back side of the 20 inches long and 3 inches wide (18 g) of the Plaster of Paris tape (Type B). The polyisocyanate was an NCO-quasi prepolymer from Example 9, but without the presence of tertiary amine catalyst. After coating with polyisocyanate, the tape was dipped in water for 5 seconds, wound and cast around TABLE 2-continued

| Designation | Example 9 | Example 10 | Example 11 |
|---|---|---|---|
| Catalyst, tertiary amine | <0.05 | 0 | 0 |
| Compressive strength (psi) | | | |
| 2% compression | 34.4 | 29.7 | 26.9 |
| 5% compression | 43.6 | 50.1 | 36.0 |
| 10% compression | 51.0 | 59.7 | 45.7 |
| 20% compression | 60.4 | 65.8 | 54.6 |

Examples 9–11 demonstrate that the addition of polyisocyanate improves the strength of fully cured Plaster of Paris cast.

EXAMPLE 12

The Plaster of Paris casts were prepared from the Plaster of Paris tape (Type B), as described in the Example 11, and the compressive strength of the cast was measured after one (1) hour of curing (Table 3). Table 3 includes compressive properties of one (1) hour cured Plaster of Paris casts.

EXAMPLE 13

The polyisocyanate modified Plaster of Paris casts was prepared as described in Example 9, and the compressive strength of the casts was measured after one (1) hour of curing (Table 3).

TABLE 3

| Designation | Example 12 | Example 13 |
|---|---|---|
| Type of Cast | PP | HPP |
| Composition (pbw) | | |
| Plaster of Paris tape, Type B | 18 | 18 |
| Polyisocyanate | 0 | 1.5 |
| Catalyst, tertiary amine | 0 | <0.05 |
| Compressive strength (psi) | | |
| 2% compression | 6.5 | 12.2 |
| 5% compression | 9.8 | 15.0 |
| 10% compression | 12.3 | 17.0 |
| 20% compression | 15.7 | 19.8 |

Examples 12–13 demonstrate that the addition of polyisocyanate to PP, according to the present invention, improves the plaster of Paris strength after only 1 hour of curing, illustrating better green strength of HPP tapes over PP tapes.

While the best mode for carrying out the invention has been described in detail, those familiar with the art to which their invention relates will recognize various alternative designs and embodiments for practicing the invention as described by the following claims.

What is claimed:

1. A casting article, the article comprised of:
   a water-curable Plaster of Paris (PP) article having a first side and a second side and having a substrate and PP material; and
   a polyisocyanate material being applied to at least one of the first and second sides of the water-curable PP to obtain a water-curable hybrid plaster-polyisocyanate (HPP) casting article.

2. The casting article of claim 1 wherein the water-curable HPP casting article is cured.

3. The casting article of claim 1 wherein the first side of the water-curable PP article is smoother than the second side and the polyisocyanate material is applied to the first side.

4. The casting article of claim 1 wherein the water-curable PP article is a water-curable PP casting tape or a water-curable PP splint and the polyisocyanate material is a polyisocyanate tape or a polyisocyanate resin.

5. The casting article of claim 4 wherein the substrate for the PP article is selected from the group consisting of cotton, glass fiber, polymeric knit, woven material and non-woven material.

6. The casting article of claim 1 wherein the weight ratio of the polyisocyanate material and the water-curable PP article is in the range of about 1:99 to about 99:1.

7. The casting article of claim 1 wherein the polyisocyanate material is selected from the group consisting of aromatic isocyanates, aliphatic isocyanates, cycloaliphatic isocyanates, isocyanate-based adducts, isocyanate-based derivatives, NCO-prepolymers, NCO-oligomers and NCO-quasi prepolymers.

8. The casting article of claim 7 wherein the polyisocyanate material has an isocyanate to active hydrogen equivalent weight ratio of greater than about 1.

9. The casting article of claim 2 wherein the polyisocyanate material is cured without a catalyst that promotes the reaction of the polyisocyanate material and water.

10. The casting article of claim 2 wherein the polyisocyanate material is cured with at least one catalyst promoting the reaction of the polyisocyanate material and water.

11. The casting article of claim 10 wherein the PP material includes the baked product of a PP paste and the at least one catalyst is added to the PP paste.

12. The casting article of claim 11 wherein the at least one catalyst does not significantly interfere with the curing of the water-curable PP article.

13. The casting article of claim 1 wherein the water-curable PP article includes at least one hardening agent and the polyisocyanate material includes at least one antifoaming agent and at least one stabilizer.

14. A casting assembly, the assembly comprised of:
    a water-curable Plaster of Paris (PP) tape having a first side and a second side and having a substrate and PP material; and
    a polyisocyanate tape having a substrate and a polyisocyanate resin,
    whereby the water-curable PP tape and the polyisocyanate tape can be contacted to obtain a water-curable hybrid plaster-polyisocyanate (HPP) casting article.

15. The casting assembly of claim 14 wherein the water-curable HPP casting article is cured.

16. The casting assembly of claim 14 further comprising a pouch for at least partially containing the water-curable PP tape and the polyisocyanate tape.

17. The casting assembly of claim 16 further comprising a foil material for at least partially separating the water-curable PP tape and the polyisocyanate tape in the pouch.

18. The casting assembly of claim 14 wherein the PP and polyisocyanate tape are dry packaged to minimize exposure to water and/or moisture.

19. The casting assembly of claim 14 wherein the water-curable PP tape and/or the polyisocyanate tape are commercially available and/or are specially designed.

20. The casting assembly of claim 14 wherein the substrate for the water-curable PP tape is selected from the group consisting of cotton, glass fiber, polymeric knit, woven material and non-woven material.

21. The casting assembly of claim 14 wherein the substrate for the polyisocyanate tape is selected from the group consisting of cotton, glass fiber, polymeric knit, woven material and non-woven material.

22. The casting assembly of claim 14 wherein the weight ratio of the polyisocyanate tape and the water-curable PP tape is in the range of about 1:99 to about 99:1.

23. The casting assembly of claim 14 wherein the polyisocyanate resin is selected from the group consisting of aromatic isocyanates, aliphatic isocyanates, cycloaliphatic isocyanates, isocyanate-based adducts, isocyanate-based derivatives, NCO-prepolymers, NCO-oligomers and NCO-quasi prepolymers.

24. The casting assembly of claim 23 wherein the polyisocyanate tape has an isocyanate to active hydrogen equivalent weight ratio of greater than about 1.

25. The casting assembly of claim 15 wherein the polyisocyanate tape is cured without a catalyst that promotes the reaction of the polyisocyanate tape and water.

26. The casting assembly of claim 15 wherein the polyisocyanate tape is cured with at least one catalyst for promoting the reaction of the polyisocyanate tape and water.

27. The casting assembly of claim 14 wherein the PP tape includes the baked-product of a PP paste and the at least one catalyst is added to the PP paste.

28. The casting assembly of claim 26 wherein the at least one catalyst does not significantly interfere with the curing of the water-curable PP tape.

29. The casting assembly of claim 14 wherein the water-curable PP tape includes at least one hardening agent and the polyisocyanate material includes at least one antifoaming agent and at least one stabilizer.

30. A method for preparing a cured hybrid plaster-polyisocyanate (HPP) casting article, the method comprised of:
providing a water-curable Plaster of Paris (PP) material having a first side and a second side and being comprised of a substrate and a PP material and a polyisocyanate material;
applying the polyisocyanate material to at least one of the first and second sides of the water-curable PP article to obtain a water-curable hybrid plaster-polyisocyanate (HPP) casting article; and
curing the water-curable hybrid plaster-polyisocyanate (HPP) casting article to obtain a cured HPP casting article.

31. The method of claim 30 wherein the applying step is comprised of spraying or coating the polyisocyanate material onto the water-curable PP article.

32. The method of claim 30 further comprising providing a PP article and baking the PP material to obtain the water-curable PP article.

33. The method of claim 32 further comprising adding at least one catalyst for promoting the reaction of isocyanates with water to the PP article prior to the baking step.

34. The method of claim 30 further comprising adding at least one catalyst for promoting reaction of isocyanates with water to the polyisocyanate material.

35. The method of claim 30 wherein the water-curable PP article is comprised of a water-curable PP tape and the polyisocyanate material is comprised of a polyisocyanate tape.

36. The method of claim 35 wherein the applying step is comprised of laminating the polyisocyanate tape onto the water-curable PP tape.

37. The method of claim 30 wherein the water-curable PP material is comprised of at least a first and second PP layer and the polyisocyanate material is comprised of at least a first and second polyisocyanate layer and further comprising prior to the curing step, applying the first polyisocyanate layer to the first PP layer, applying the second PP layer to the first polyisocyanate layer, and applying the second polyisocyanate layer to the second PP layer.

\* \* \* \* \*